(12) United States Patent
Buchwald et al.

(10) Patent No.: US 10,222,340 B2
(45) Date of Patent: Mar. 5, 2019

(54) INSPECTION DEVICE FOR CONTAINER CLOSURES

(71) Applicant: KHS GmbH, Dortmund (DE)

(72) Inventors: Carsten Buchwald, Bad Breisig (DE); Jürgen-Peter Herrmann, Rosenheim (DE); Marius Michael Herrmann, Rosenheim (DE); Wolfgang Schorn, Hönningen (DE); Xiang Zhang, Wetter (DE)

(73) Assignee: KHS GmbH, Dortmund (DE)

( * ) Notice: Subject to any disclaimer, the term of this patent is extended or adjusted under 35 U.S.C. 154(b) by 186 days.

(21) Appl. No.: 15/316,326

(22) PCT Filed: May 7, 2015

(86) PCT No.: PCT/EP2015/060061
§ 371 (c)(1),
(2) Date: Dec. 5, 2016

(87) PCT Pub. No.: WO2015/185318
PCT Pub. Date: Dec. 10, 2015

(65) Prior Publication Data
US 2018/0038804 A1    Feb. 8, 2018

(30) Foreign Application Priority Data

Jun. 5, 2014 (DE) .................. 10 2014 107 915

(51) Int. Cl.
*G01N 21/90* (2006.01)
*G01N 21/88* (2006.01)

(52) U.S. Cl.
CPC ..... *G01N 21/9054* (2013.01); *G01N 21/8806* (2013.01); *G01N 21/909* (2013.01); *G01N 2021/8845* (2013.01)

(58) Field of Classification Search
CPC .......... G01N 21/9054; G01N 21/8806; G01N 21/909; G01N 2021/8845
See application file for complete search history.

(56) References Cited

U.S. PATENT DOCUMENTS

| 4,914,289 A | 4/1990 | Nguyen et al. |
| 5,563,736 A | 10/1996 | Lewis |
| 5,592,286 A | 1/1997 | Fedor |
| 6,122,048 A * | 9/2000 | Cochran ............ G01N 21/8806 250/223 B |
| 6,643,009 B2 * | 11/2003 | Takakusaki ............... B67B 3/26 356/239.4 |

(Continued)

FOREIGN PATENT DOCUMENTS

| DE | 195 14 271 | 10/1996 |
| DE | 196 34 881 | 2/1998 |
| DE | 10 2007 008 619 | 8/2008 |

(Continued)

*Primary Examiner* — Thai Q Tran
*Assistant Examiner* — Christopher Braniff
(74) *Attorney, Agent, or Firm* — Occhiuti & Rohlicek LLP

(57) ABSTRACT

An inspection device for inspecting screw-closures on bottles includes a rotationally-symmetric lens disposed above a bottle's screw-closure and having a convex portion and a flat aspheric portion, a first lighting-unit for illuminating the screw-closure, and a camera located above the lens and connected to an image processor.

17 Claims, 3 Drawing Sheets

(56) References Cited

U.S. PATENT DOCUMENTS

2004/0150815 A1* 8/2004 Sones ............... G01N 21/9054
356/239.4

FOREIGN PATENT DOCUMENTS

| EP | 1 270 433 | 1/2003 |
|----|-----------|--------|
| JP | 2002 323 456 | 11/2002 |
| WO | WO03/002992 | 1/2003 |

* cited by examiner

INSPECTION DEVICE FOR CONTAINER CLOSURES

RELATED APPLICATIONS

This is the national stage under 35 USC 371 of PCT/EP2015/060061, filed on May 7, 2015, which claims the benefit of the Jun. 5, 2014 priority date of German application DE 1020014107915.9, the contents of which are herein incorporated by reference.

FIELD OF INVENTION

The invention relates to container processing, and in particular, to inspection of closures.

BACKGROUND

In the beverage industry, it is customary to distribute beverages in glass or plastic bottles that have been capped with closures.

These closure are typically screw-type closures made of a variety of materials, most commonly metal or plastic. A typical closure has a more or less flat surface at its top that spans the bottle's mouth. This flat surface forms a roof over a cylindrical that is aligned to be coaxial with the bottle's axis.

The closure also typically has security elements for enabling a consumer to detect product tampering. These security elements can be configured as one piece with the closure element, with a ring or engagement teeth. They can also toe implemented as a separate head label, a sleeve, or some other arrangement, and as an additional equipment element interacting with the closure element.

After bottles have been filled and closed, it is prudent to inspect the bottles to make sure that they have been correctly closed. Inspected features range from, the most basic, such as the presence of a closure in the first place, to more subtle features, such as the closure positions, the presence and quality of securing elements, the presence and alignment of decorative elements, and the presence of any damage, such as cracks.

During the inspection of a closure, and in particular of a screw closure made of plastic, such as polyethylene or polypropylene, it is useful to inspect the entire mouth region and a vertical segment of the container neck, as well as the whole of the closure material. The data from this inspection serves to screen for defective containers or container closures, and, as appropriate, to optimize the closing process.

As used herein, "closure system" means the complete desired end arrangement of all the elements required to correctly close the bottle. These would include the actual cover, as the closure element, the decorative elements, the security element, and contact surfaces at the container neck, adjacent to and, as appropriate, in functional interaction with the closure element, such as a neck ring.

It is also desirable to carry out the inspection without any spatial movement but to nevertheless inspect 360° around the bottle. To promote high performance capacities and transport speeds, it is desirable to maintain a continuous inspection process.

SUMMARY

An object of the invention is that of providing a device that improves detection and evaluation capability for closure systems.

According to the invention, the object is solved by a device for the inspection of closure systems of containers with an optical lens configured as a rotationally symmetrical flat aspherical lens.

By means of this embodiment, imaging errors that occur with a spherical lens in the form of a flat convex lens or meniscus lens, can be reduced or even eliminated altogether. Advantages of this solution are lower cost, easy application, and high reliability.

In a rotationally symmetric flat aspherical lens, one passage side of the lens is flat, and the other passage side of the lens has its absolute high point on the lens axis. The course of the surface of the upper side can be described by an aspherical surface coarse.

The aspherical surface course is described on a conic section that passes into a course that is defined by a power series of a higher order. The equation that defines the sagittal of an aspherical surface according to DIN ISO 10110-12 is as follows:

$$z(r) = \underbrace{\frac{r^2}{R\left(1 + \sqrt{1 - (1+k)\left(\frac{r}{R}\right)^2}\right)}}_{I} + \underbrace{A_4 r^4 + A_6 r^6 + \ldots}_{II}$$

where:
I=Equation portion of the conic section
II=Equation portion as power series for deformations of a higher order
z=Sagitta
r=Distance interval perpendicular to the axis (incidence height)
R=Vertex radius
k=Conical constant
A4, A6 . . . =Aspherical parameters According to the invention, the aspherical surface course comprises a surface course that is convex in the lens axis, as defined by the lower-order term, i.e. the portion of the equation marked "I" and at least one concave or flat surface course defined by one or more higher order terms, namely from the portion of the equation portion marked "II".

By way of this configuration, light beams that are reflected from the lower edge of the material being observed are refracted by the aspherical part of the lens, which, thanks to its specially adapted surface course, allows it to prevent spherical aberrations and likewise to represent deep observation regions of the closure's side surface in sharp focus.

In a preferred embodiment the surface course is configured in such a way that ail the light beams are bundled at the same intersection point. This achieves an optimum sharpness of focus for the image, even for beams that have been reflected from the lower side surface regions, i.e. those furthest removed from the lens's underside.

Due to the fact that the lens is rotationally symmetrical, it can be divided in cross-section into horizontal sections which differ through its surface courses. An example is provided in the description following hereinafter of a special embodiment of the rotationally symmetric flat aspherical lens.

An improved embodiment consists of the fact that, with the lighting device according to the invention, which is preferably configured as an LED lighting device, light spectra of different wavelengths can be emitted.

In this situation, the ideal light spectrum to be chosen is dependent on the container and closure properties or the refraction behavior of the aspherical lens.

In a preferred embodiment, the lighting can in this way be especially adjusted to different materials and colors, for example a security ring which is different from the closure material, in order to achieve an optimum image quality. For this purpose, the lighting unit has, for example, regions (in particular concentric regions) which can emit light of different wavelengths and/or intensities. Accordingly, for example, for the detection of damage or cracks in the closure side wall, one of the basic bodies of a very dark screw closure can be irradiated differently (more intensively) than the neck ring and/or the transition region to the neck ring in order to detect location and damage in this region, or a part region of the closure element may comprise a very light and highly reflective décor region, which, if necessary, must be irradiated with a special monochrome light, and deeper lying regions of the closure side surface and/or of a deep security ring must be irradiated with a light with a wavelength which differs from this.

It can be of further advantage for the data evaluation if the lighting unit irradiates the closure system in such a way that, in the convex lens section, predominantly light (beams) impinge with a first wavelength, and light (beams) with a second wavelength impinge into the aspherical lens section.

BRIEF DESCRIPTION OF THE FIGURES

These and other features of the invention will be apparent from the following detailed description and the accompanying figures, in which.

DETAILED DESCRIPTION

Figure 1:
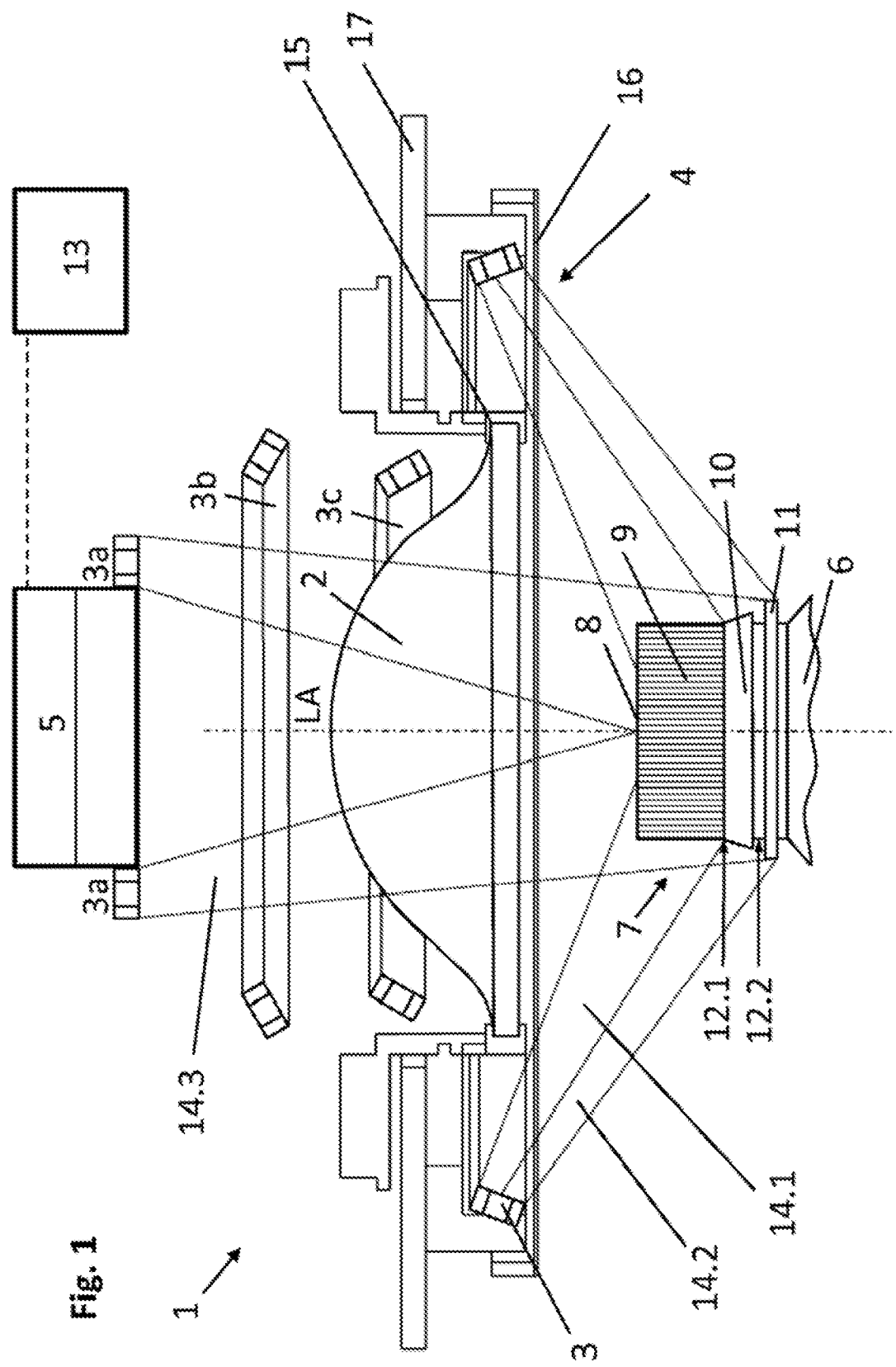
FIG. 1 shows a side view of an inspection device.

Referring to FIG. 1, an inspection device 1 features an aspherical lens 2, a first lighting-unit 3, and a carrying-and-holding device, hereafter referred to as a holder 4.

The first lighting-unit 3 is arranged concentrically about the lens 2 and about the lens axis A. In some embodiments, the first lighting-unit 3 is implemented using light-emitting diodes. The holder 4 carries or holds both the first lighting-unit 3 and the lens 2.

Above the lens 2, and in alignment with it, is an image-detection unit, which in the illustrated embodiment includes a camera 5. The camera 5 connects to an image processor 13.

Also shown in FIG. 1 is a bottle 6 having a closure 7 to be inspected. The closure 7 is disposed on the bottle's mouth and closure region.

The closure 7 includes a head surface 8, a securing ring 10, and a side surface 9 between the head surface 8 and the securing ring 10. The side surface 9 typically has a threaded section and a toothed or roughed surface. The securing ring 10 generally has inwardly directed engagement teeth to deter product tampering.

The closure 7 is configured as one piece with the securing ring 10 as a lower end. The closure's surface changes from one region to the next. In the region of the side surface 9, it has longitudinal vertical grooves. In the region of the securing ring 10, it is smooth and inclined slightly obliquely outwards.

Just beneath the securing ring 10 is the container's neck ring 11. From the neck ring 11 downward, one traverses the container's neck, its shoulder, its body, and ultimately, its base.

The holder 4 includes a clamping groove 15, a cover disk 16, and a securing flange 17. The clamping groove 15 permits detection and positioning of the lens's edge. The securing flange 17 connects and fixes the entire holder 4 to adjacent device elements. And the cover disk 16 provides support for the first lighting-unit 3.

Ideally, the first lighting-unit 3 is arranged above the lower cover disk 16. This permits light from the first lighting-unit 3 to bypass the lens 2 and to impinge directly onto the closure 7.

A closure system has first and second transition regions 12.1, 12.2. The first transition region 12.1 is a ring between the closure side surface 9 and the securing ring 10. Being made of PE material, or polyethylene, it appears somewhat lighter. The second transition region 12.2 is a ring gap between the lower edge of the securing ring 10 and the upper edges of the neck ring 11. When the closure element 7 is correctly placed, the second transition region 12.2 has a height that remains constant as one proceeds in the circumferential direction.

The first lighting-unit 3 emits first and second light beams 14.1, 14.2 at corresponding first and second wavelengths onto the bottle's closure 7. The particular values of wavelength are optimally adjusted based on specific requirements.

The first light-beam 14.1 reflects off of the closure's side surface 9 and off of the first transition region 12.1. The second light-beam 14.2 reflects off of the securing ring 10 or, as appropriate, the neck ring 11 and the second transition region 12.2. The rotationally symmetric flat aspherical lens 2, which is arranged perpendicularly above, conveys these beams to the camera 5.

The first transition-region 12.1 is particularly important because of its relevance to safety. Some embodiments thus irradiate and inspect the first transition-region 12.1 separately, inasmuch as light of an individual wavelength and/or intensity is selected.

Because of the lens's profile, which is convex, flat, and concave in different regions, the first and second light beams 14.1, 14.2 meet at a common intersection point. As a result, the camera 5 receives a particularly sharp and undistorted image.

Some embodiments, including that shown in FIG. 1, include a second lighting-unit 3a that provides third light-beams 14.3. These third light-beams 14.3 travel through the lens 2 onto the closure's head, surface 8, which then reflects them into the camera 5. The second lighting-unit 3a is arranged for this purpose above the first lighting-unit 3.

Ideally, the second lighting-unit 3a is at the height of the camera 5. However, as shown in FIG. 1, a third lighting unit 3b or a fourth lighting unit 3c can be used instead of the second lighting-unit 3a. These function in the same way as the second lighting-unit 3a but are located slightly closer to the first lighting-unit 3. In each case, the second, third, or fourth lighting units 3a, 3b, 3c are arranged as an LED ring concentric with the lens axis LA.

The camera 5 ultimately provides the recorded image to the electronic image processor 13, which then converts it into polar coordinates and evaluates it.

Figure 2:
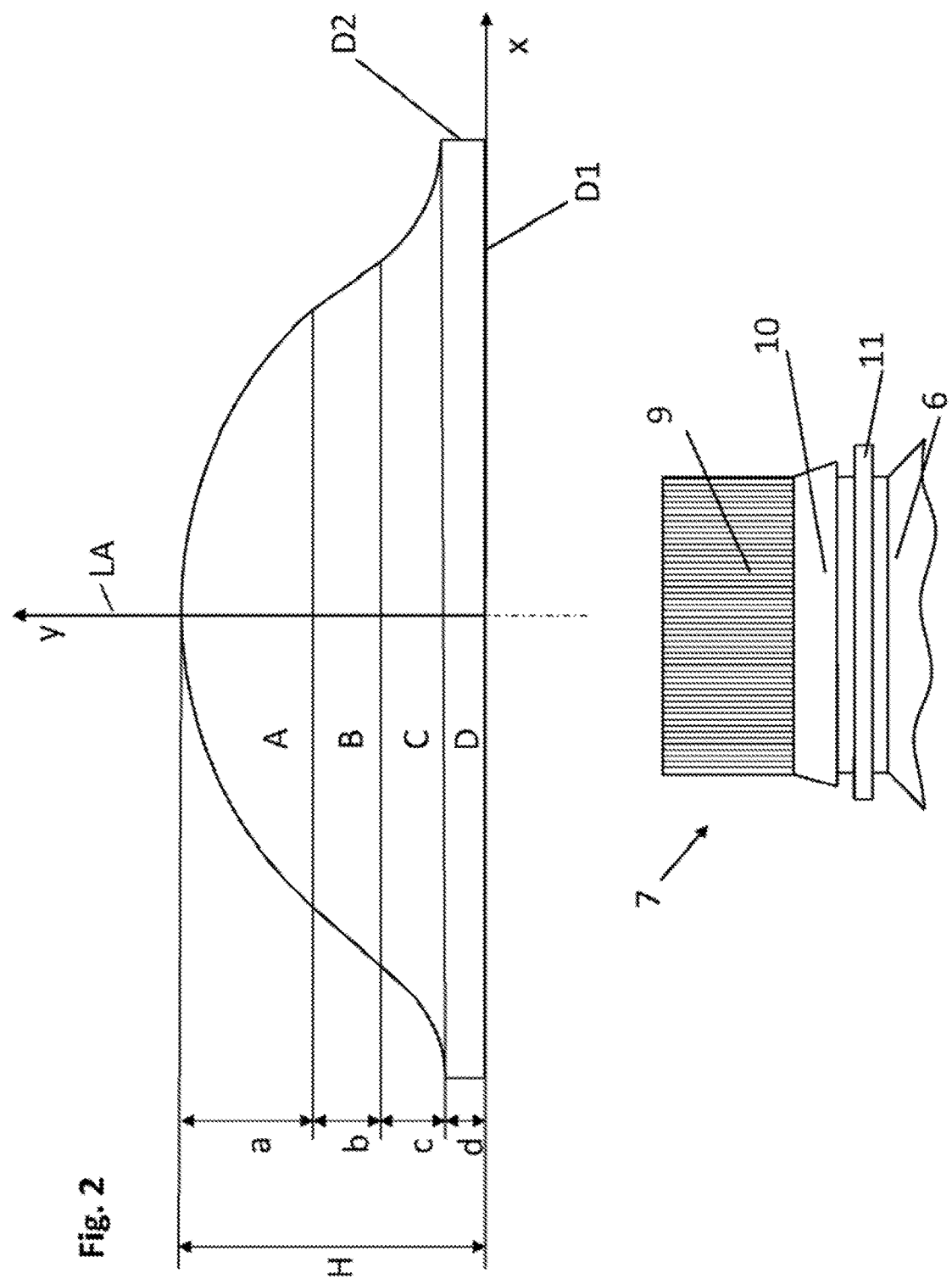
FIG. 2 shows a side view of an aspherical lens from the inspection device of FIG. 1.

In a second embodiment, shown in FIG. 2, an aspherical lens 2 of height H includes: a first lens-region A having a first height a, a second lens-region B having a second height b, a third lens-region C having a third height c, and a fourth lens-region D having a fourth height d. The sum of the first through fourth heights a-d equals the lens's height H.

The first, lens-region A has a convex surface, which is described in the lowest order term, marked "I," in the DIN ISO 10110-12 equation. The second lens region B, which is just below the first lens-region A, has a flat surface. The third lens region C, which is just below the second lens-region B, has a concave surface. The second and third lens-regions B, C together form the aspherical surface region of the lens 2, and can be described by the higher-order terms marked "II" in the DIN ISO 10110-12 equation.

The fourth lens region D, which includes an underside D1 and vertical outer side surface D2 forms the lens's flange, or mounting. This enables the lens 2 to be positioned and secured. The vertical outer side surface D2 does not, as a rule, contribute to the beam's guidance. This is because, under normal circumstances, beams are neither introduced nor emitted through the vertical outer side surface D2.

Depending on the object of the inspection, one of the second and third lens regions B, C may not be necessary. Furthermore, in some embodiments, the lowest region of the second and third lens regions B, C can be configured to be large for enough to also accommodate a suitable carrier or mounting to be able to fix the lens in a secure position. In these embodiments, the fourth lens region D becomes unnecessary. The bottom surface in this case would then be the underside of the lower of the second and third lens region B, C.

In some embodiments, the containers are held horizontally instead of with their head facing upwards. In such cases, the foregoing device is oriented accordingly with no change in operation. In particular, FIG. 1, if viewed in portrait mode instead of landscape mode, illustrates this horizontal embodiment.

The foregoing apparatus is thus able to use a single lens above the path of the container and a single image-detection device, in particular a camera, to detect and inspect a closure system for a screw closure cap, including its neck ring and ail elements, contours, and geometries arranged from the neck ring on up to the top of the cap. This can foe carried out with high quality and reliability.

Although the apparatus can make use of pulsed light sources, such pulsed light sources are not required.

A particularly advantageous embodiment uses an LED lighting system with the specifically aimed region-by-region lighting of the closure system that has been tuned to the respective surfaces and their optical effects.

Figure 3:
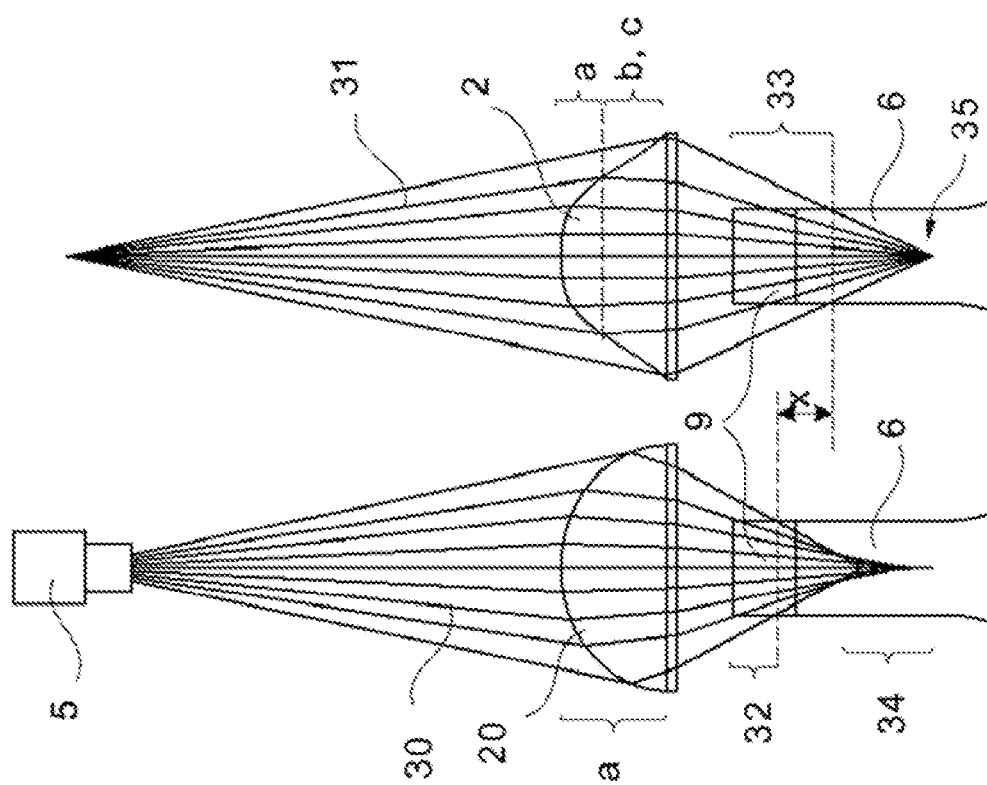
FIG. 3 compares rays passing through a spherical lens with rays passing through an aspherical lens.

FIG. 3 shows a beam path 30 through a spherical lens 20 shown in comparison with a beam path 31 through the aspherical lens 2. It can be seen in particular that the beam diffraction in the aspherical region b, c of the lens 2 allows an inspection image 33 enlarged by the path x in relation to the smaller inspection image 32 of the spherical lens 20. As a result, the aspherical lens 2 makes it possible to obtain a deeper view along the container's axial direction and therefore in the axial direction of the larger inspection image 33.

It is also apparent from FIG. 3 that a focal point 35 of the aspherical lens 2 is formed much more sharply. This results in higher image quality and sharpness of focus. In contrast, a focal point 34 of the spherical lens 20 is noticeably more scattered. This results in a more diffuse image.

Having described the invention, and a preferred embodiment thereof, what is claimed as new and secured by Letters Patent is:

1. An apparatus comprising an inspection device for inspecting a screw-closure on a bottle, said apparatus comprising a lens, a first lighting-unit, a camera, and an image processor, wherein said lens has a lens axis, wherein said lens is disposed vertically above said closure, wherein said camera is located vertically above said lens, wherein beam bundling of light provided by said first lighting-unit takes place in a direction leading towards said camera, wherein said camera connects to said image processor, wherein said lens is rotationally symmetric, wherein said lens comprises a lens surface, wherein said lens comprises first lens-region and a second lens-region, wherein said first lens-region defines a convex portion of said lens surface, and wherein said second lens-region defines a flat aspheric portion of said lens surface, whereby said lens is an aspheric lens, wherein said lens has a cross-section that comprises a first layer, a second layer, and a third layer, wherein said first layer is an uppermost layer, wherein said second layer is below said first layer and above said third layer, wherein said first layer defines a convex portion of said lens surface, wherein said second layer defines a non-convex flat portion of said lens surface, and wherein said third layer defines a concave portion of said lens surface.

2. The apparatus of claim 1, wherein said second lens-region comprises a third lens-region and a fourth lens-region that are adjacent to each other, wherein said fourth lens-region comprises a convex surface and wherein said third lens-region comprises a flat surface.

3. The apparatus of claim 1, wherein a sum of heights of said layers equals the height of said lens.

4. The apparatus of claim 1, wherein said first lighting-unit is a ring of lights.

5. The apparatus of claim 1, wherein said first lighting-unit comprises a first region that emits first light having a first wavelength and a second region that emits second light having a second wavelength.

6. The apparatus of claim 1, wherein said first lighting-unit comprises a first region that emits first light and a second region that emits second light, wherein said first light has a first wavelength, wherein said second light has a second wavelength, wherein said first lighting-unit directs said first light to said first lens-region, wherein said first lighting-unit directs said second light to said second lens-region, wherein said first lighting-unit directs said first light to avoid said second lens-region, and wherein said first lighting-unit directs said second light to avoid said first lens-region.

7. The apparatus of claim 1, wherein said first lighting-unit comprises a first region that emits first light and a second region that emits second light, wherein said first light has a first wavelength, wherein said second light has a second wavelength, wherein said first lighting-unit directs said first light to a first surface of a closure system disposed beneath said lens, wherein said first lighting-unit directs said second light to a second surface of said closure system, wherein said first lighting-unit avoids directing said first light to said second surface, and wherein said first lighting-unit avoids directing said second light to said first surface.

8. The apparatus of claim 1, wherein said inspection device is configured to inspect a closure having a closure diameter, wherein said lens has a maximum outer diameter, wherein said maximum outer diameter is at least two and a half times said closure diameter.

9. The apparatus of claim 1, wherein said first lighting-unit comprises a plurality of light-emitting fields.

10. The apparatus of claim 1, further comprising a plurality of diodes, wherein said diodes are arranged in an annulus centered at said lens axis, wherein said diodes are a constituent of said first lighting-unit.

11. The apparatus of claim 1, further comprising a second lighting-unit that is offset from said first lighting device in a direction away from said lens.

12. The apparatus of claim 1, wherein said first lighting-unit comprises first and second concentric regions, wherein said first concentric region emits first light and said second concentric region that emits second light, wherein said first light has a first wavelength, wherein said second light has a second wavelength, wherein said first lighting-unit directs said first light to said first lens-region, wherein said first lighting-unit directs said second light to said second lens-region, wherein said first lighting-unit directs said first light to avoid said second lens-region, and wherein said first lighting-unit directs said second light to avoid said first lens-region.

13. The apparatus of claim 1, wherein said first lighting-unit comprises a first region that emits first light and a second region that emits second light, wherein said first light has a first intensity, wherein said second light has a second intensity, wherein said first lighting-unit directs said first light to a first surface of a closure system disposed beneath said lens, wherein said first lighting-unit directs said second light to a second surface of said closure system, wherein said first lighting-unit avoids directing said first light to said second surface, and wherein said first lighting-unit avoids directing said second light to said first surface.

14. The apparatus of claim 1, wherein said inspection device further comprises a holder, wherein said holder is configured to support said lens and said first lighting-unit.

15. The apparatus of claim 1, wherein said camera is on a first level, wherein said inspection device further comprises a second lighting-unit, wherein said second lighting-unit is disposed on said first level.

16. An apparatus comprising an inspection device for inspecting a screw-closure on a bottle, said apparatus comprising a lens, a first lighting-unit, a camera, and an image processor, wherein said lens has a lens axis, wherein said lens is disposed vertically above said closure, wherein said camera is located vertically above said lens, wherein beam bundling of light provided by said first lighting-unit takes place in a direction leading towards said camera, wherein said camera connects to said image processor, wherein said lens is rotationally symmetric, wherein said lens comprises a lens surface, wherein said lens comprises first lens-region and a second lens-region, wherein said first lens-region defines a convex portion of said lens surface, and wherein said second lens-region defines a flat aspheric portion of said lens surface, whereby said lens is an aspheric lens, wherein said first lighting-unit comprises first and second regions that emit corresponding first and second light having corresponding first and second intensities, said first and second regions having a common center, wherein said first lighting-unit directs said first light to said first lens-region, wherein said first lighting-unit directs said second light to said second lens-region, wherein said first lighting-unit directs said first light to avoid said second lens-region, and wherein said first lighting-unit directs said second light to avoid said first lens-region.

17. An apparatus comprising an inspection device for inspecting a screw-closure on a bottle, said apparatus comprising a lens, a first lighting-unit, a camera, and an image processor, wherein said lens has a lens axis, wherein said lens is disposed vertically above said closure, wherein said camera is located vertically above said lens, wherein beam bundling of light provided by said first lighting-unit takes place in a direction leading towards said camera, wherein said camera connects to said image processor, wherein said lens is rotationally symmetric, wherein said lens comprises a lens surface, wherein said lens comprises first lens-region and a second lens-region, wherein said first lens-region defines a convex portion of said lens surface, and wherein said second lens-region defines a flat aspheric portion of said lens surface, whereby said lens is an aspheric lens, wherein said inspection device further comprises a cover disk, a flange, and a groove, wherein said groove is configured to position an edge of said lens, wherein said cover disk supports said first lighting-unit, and wherein said securing flange secures a holder that comprises said flange and groove to another component of said inspection device.

* * * * *